United States Patent
Matsumoto et al.

(10) Patent No.: US 6,881,872 B2
(45) Date of Patent: Apr. 19, 2005

(54) LESS COLORED TRANS-1,3-DICHLOROPROPENE AND PROCESS FOR ITS PRODUCTION

(75) Inventors: Tomoko Matsumoto, Tokyo (JP); Tateo Nakano, Ibaraki (JP); Yutaka Yokoyama, Ibaraki (JP)

(73) Assignee: Asahi Glass Company, Limited, Tokyo (JP)

( * ) Notice: Subject to any disclaimer, the term of this patent is extended or adjusted under 35 U.S.C. 154(b) by 50 days.

(21) Appl. No.: 10/397,516

(22) Filed: Mar. 27, 2003

(65) Prior Publication Data

US 2003/0164284 A1 Sep. 4, 2003

Related U.S. Application Data

(63) Continuation of application No. PCT/JP01/08366, filed on Sep. 26, 2001.

(30) Foreign Application Priority Data

Sep. 27, 2000 (JP) ........................................ 2000-293918

(51) Int. Cl.$^7$ ........................ C07C 17/383; C07C 17/38

(52) U.S. Cl. ........................ 570/238; 570/181; 570/216; 570/234; 570/236; 570/231

(58) Field of Search ................................. 570/181, 238, 570/216, 234, 236, 231

(56) References Cited

U.S. PATENT DOCUMENTS 3,914,167 A   10/1975   Ivy et al.

FOREIGN PATENT DOCUMENTS

JP   39-25105   11/1964

Primary Examiner—Elvis O. Price
(74) Attorney, Agent, or Firm—Oblon, Spivak, McClelland, Maier & Neustadt, P.C.

(57) ABSTRACT

Less colored trans-1,3-dichloropropene and a process for producing it, are presented.

A composition comprising cis-1,3-dichloropropene, trans-1,3-dichloropropene and $C_6$ compounds, is subjected to a distillation step and to a step of reacting chlorine or bromine, to remove cis-1,3-dichloropropene as a low boiling component, and then the residue is distilled to remove the chlorinated $C_6$ compounds as a high boiling component and to obtain trans-1,3-dichloropropene as a low boiling component.

17 Claims, 1 Drawing Sheet

LESS COLORED TRANS-1,3-DICHLOROPROPENE AND PROCESS FOR ITS PRODUCTION

TECHNICAL FIELD

The present invention relates to trans-1,3-dichloropropene useful as e.g. an intermediate for pharmaceuticals or agricultural chemicals.

BACKGROUND ART 1,3-Dichloropropene has isomers i.e. cis-1,3-dichloropropene (hereinafter referred to as a cis-isomer) and trans-1,3-dichloropropene (hereinafter referred to as a trans-isomer) and is known as a compound useful in the medical and agricultural fields.

Heretofore, as a method for separating such a cis-isomer and a trans-isomer, e.g. JP-B-53-15484 discloses a process wherein a reaction product obtainable by a reaction of propene with chlorine, is distilled to obtain 3-chloropropene, and then, from the bottom after the distillation, the cis-isomer and the trans-isomer of 1,3-dichloropropene are separated. Namely, in the above bottom, residual substances such as 1,3-dichloropropene and $C_6$ olefins, are contained as by-products of the reaction. Firstly, chlorine or bromine is reacted to the bottom to selectively halogenate the $C_6$ olefins, and then, this bottom is distilled to remove a light component having a boiling point lower than 1,3-dichloropropene. Thereafter, the bottom is further distilled to remove the halogenated $C_6$ olefins as a high boiling component and to fractionate 1,3-dichloropropene as a low boiling component. And, such 1,3-dichloropropene is further distilled to separate the trans-isomer as a high boiling component and the cis-isomer as a low boiling component.

In the above process, a lower boiling component and a higher boiling point component than the cis-isomer and the trans-isomer, are sequentially removed by distillation, and thereafter, the cis-isomer and the trans-isomer are fractionated, and this fraction is distilled to separate the cis-isomer and the trans-isomer. In such a case, the trans-isomer has a boiling point higher than the cis-isomer, and accordingly, the trans-isomer is separated as a high boiling component. Accordingly, the trans-isomer as the high boiling component, has had a problem that distillation residues are likely to be included, or the purity is low and it contains coloring components substantially.

Further, in order for the trans-isomer to be used as a material for e.g. an intermediate for pharmaceuticals, an intermediate for agricultural chemicals or an intermediate for functional materials, it is required to have a Hazen color number (APHA) of at most 20. Whereas, the trans-isomer obtainable by the conventional process has had a problem that it is substantially densely colored with its APHA being about 500.

Namely, it is an object of the present invention to solve the above problem and to effectively obtain a less colored trans-isomer of high purity.

DISCLOSURE OF THE INVENTION

To solve the above-mentioned problem, the present invention provides a process for producing less colored trans-1,3-dichloropropene of high purity, which comprises distilling the following composition (II) obtainable from the following composition (I), to remove a component containing chlorinated or brominated $C_6$ compounds (compounds X), as a high boiling component, and to obtain trans-1,3-dichloropropene as a low boiling component:

Composition (I): A composition comprising cis-1,3-dichloropropene, trans-1,3-dichloropropene and $C_6$ compounds;

Composition (II): A composition which is the following composition (IIA) and/or the following composition (IIB);

Composition (IIA): A composition which is obtainable by distilling the composition (I) to remove a low boiling component containing cis-1,3-dichloropropene and then reacting chlorine or bromine to the residual high boiling component, and which comprises trans-1,3-dichloropropene and chlorinated or brominated $C_6$ compounds (compounds X);

Composition (IIB): A composition which is obtainable by reacting chlorine or bromine to the composition (I), followed by distillation to remove a low boiling component containing cis-1,3-dichloropropene, and which comprises trans-1,3-dichloropropene and chlorinated or brominated $C_6$ compounds (compounds X).

The present invention provides less colored trans-1,3-dichloropropene having a Hazen color number (APHA) of at most 200.

BEST MODE FOR CARRYING OUT THE INVENTION

Now, the present invention will be described in detail with reference to FIGS. 1 and 2.

The process of the present invention comprises two distillation steps and one step of reacting chlorine or bromine. More specifically, the composition (I) is subjected to one distillation (first distillation) step and one step of reacting chlorine or bromine, to obtain the composition (II), and then, the composition (II) is subjected to the second time distillation (second distillation) step to obtain the less colored trans-isomer in high purity.

The composition (I) to be used in the present invention comprises the cis-isomer, the trans-isomer and $C_6$ compounds. The $C_6$ compounds are meant for compounds having six carbon atoms. The composition (I) in the present invention is preferably a reaction product of propene with chlorine, or a residue having 3-chloropropene separated from such a reaction product. The latter residue is more preferred. Specifically, a bottom having 3-chloropropene separated by distillation from the reaction product of propene with chlorine, is preferably employed. The $C_6$ compounds contained in such a reaction product or in such a residue, may, for example, be chlorinated hydrocarbons having 6 carbon atoms, such as chlorohexane and chlorohexadiene. The chlorinated hydrocarbons include saturated and unsaturated ones. The chlorinated hydrocarbons usually comprise two or more types differing in the bonding position of the chlorine atom or in the position of the carbon-carbon unsaturated bond. Further, the composition (I) of the present invention may contain other components such as $C_3$ compounds. The $C_3$ compounds are meant for compounds having 3 carbon atoms and may, for example, be $C_3$ chlorinated hydrocarbons such as 1,3-dichloropropane, 1,2- dichloropropane and 3,3-dichloropropane. Also in this case, the chlorinated hydrocarbons include saturated and unsaturated ones.

In the composition (I) in the present invention, the content of the cis-isomer is preferably from 10 to 40 mass %, and the content of the trans-isomer is preferably from 10 to 40 mass %. The content of the $C_6$ compounds is preferably at most 20 mass %. Further, in a case where $C_3$ compounds are contained, such a content is preferably at most 60 mass % in the composition (I).

In the present invention, the composition (I) is subjected to a step of reacting chlorine or bromine and a distillation step, to obtain the composition (II). Hereinafter, with respect to the step of reacting chlorine or bromine, description will be made with reference to chlorine, but it should be understood that the present invention is not limited to the case of chlorine.

Figure 1:
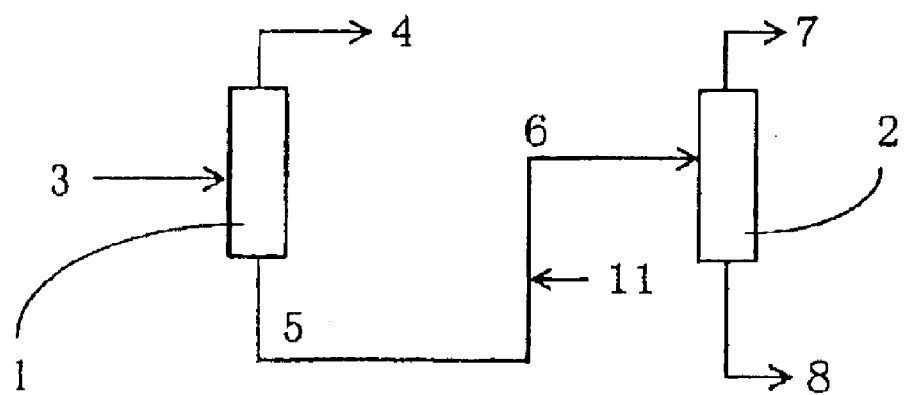
FIG. 1 is a flowchart illustrating one embodiment of the process of the present invention.

FIG. 1 shows an embodiment of the process of the present invention in a case where the composition (IIA) is obtained as the composition (II).

In this process, the composition (IIA) 6 is obtained by distilling (first distillation, hereinafter referred to as distillation A) of the composition (I) 3 in a distillation tower 1 to remove a low boiling component 4 containing the cis-isomer, and then, reacting chlorine to the residual high boiling component 5. In a case where the composition (I) 3 contains $C_3$ compounds or low boiling other components, such $C_3$ compounds or low boiling other components can be removed together with the cis-isomer, as a low boiling component 4.

In distillation A, the distillation temperature of the low boiling component 4 is preferably from 20 to 120° C., more preferably from 60 to 80° C. The pressure (the gauge pressure, the same applies hereinafter) is preferably from 0 to 1013 hPa, more preferably from 80 to 300 hPa. Distillation A is usually carried out by using a distillation tower 1, and a distillation tower having preferably from 20 to 50 plates, more preferably from 30 to 50 plates, may be employed. Further, the first distillation system is not particularly limited, and a batch system or a continuous system may optionally be employed.

In the residual high boiling component 5 after distillation A, the trans-isomer and $C_6$ compounds will be contained. Depending upon the composition (I) 3 to be used, other high boiling components, coloring components, or distillation residues to be included from the distillation apparatus, etc., may sometimes be contained in the high boiling component 5.

Then, chlorine is reacted to the high boiling component 5. As a result, the composition (IIA) will be obtained. A chlorinated $C_6$ compound (compound (X)) will be formed by addition of chlorine to an unsaturated bond in a carbon-carbon unsaturated bond-containing compound (a $C_6$ compound) such as chlorohexadiene contained in the high boiling component 5, or by substituting chlorine for the C—H moiety which may be present in such a $C_6$ compound. To react chlorine to the high boiling component 5, usually, chlorine gas may be blown into the high boiling component 5.

In the present invention, the step of reacting chlorine is preferably carried out from 0 to 100° C., more preferably from 20 to 60° C., and usually, the reaction will readily proceed at room temperature (around 25° C.). If the temperature for reacting chlorine is lower than 0° C., the reaction speed tends to be slow, whereby it will be required to make the reaction region wide in the step of reacting chlorine in the installation for carrying out the process of the present invention, such being disadvantageous economically and from the viewpoint of efficiency. On the other hand, if it is higher than 100° C., the trans-isomer is likely to be chlorinated, whereby the yield of the trans-isomer is likely to decrease.

The step of reacting chlorine in the present invention can be carried out under any pressure ranging from low pressure to high pressure. Usually, it is preferably carried out at atmospheric pressure. The amount of chlorine to be reacted is preferably from 0.5 to 5.0 times by mol, more preferably from 1.0 to 2.0 times by mol, relative to the $C_6$ compounds. If the amount of chlorine is less than 0.5 time by mol to the $C_6$ compounds, chlorination of the $C_6$ compounds will be inadequate, whereby the trans-isomer of high purity may not be obtainable. On the other hand, if it is more than 5.0 times by mol, the amount of the trans-isomer to be chlorinated tends to increase, whereby the yield of the trans-isomer is likely to be substantially decreased.

In the present invention, the chlorine to be used in the step of reacting chlorine may be liquid or gas.

In the step of reacting chlorine in the present invention, it is likely that a reaction to convert C—H to C—Cl takes place to form hydrogen chloride. When hydrogen chloride is formed, it is preferred to apply common post treatment such as flushing, dissipation, adsorption, neutralization or the like, to the composition having chlorine reacted, to obtain the composition (IIA) 6 having hydrogen chloride removed.

Figure 2:
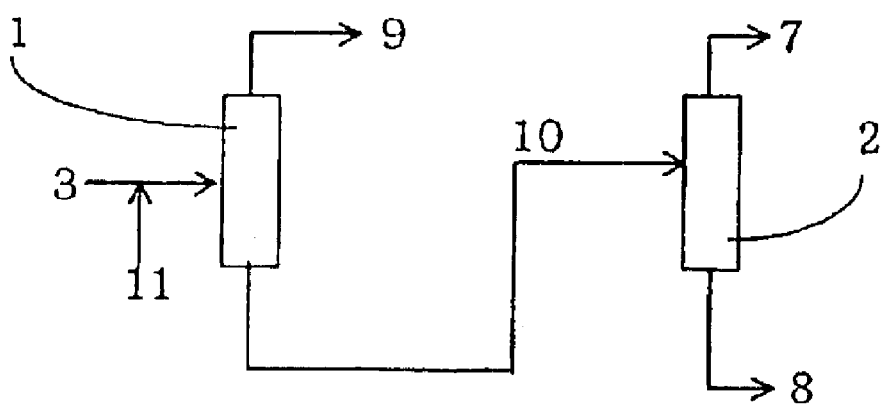
FIG. 2 is a flowchart illustrating one embodiment of the process of the present invention.

Now, an embodiment of the process of the present invention wherein the composition (IIB) will be obtained as the composition (II), will be shown in FIG. 2.

In this process, after reacting chlorine or bromine to the composition (I) 3, distillation in a distillation tower 1 (first distillation, hereinafter referred to as distillation B) is carried out. The step of reacting chlorine can be carried out in the same manner as described for the process of obtaining the above composition (IIA) 6. Further, the operation of distillation B can be carried out in the same manner as distillation A. By distillation B, a low boiling component 9 containing the cis-isomer will be removed. Further, in a case where the $C_3$ compounds or the like is contained in the composition (I) 3, such $C_3$ compounds or the like will be removed together with the cis-isomer, as a low boiling component 9. In the composition (IIB) 10 to be obtained as a high boiling component, the trans-isomer and the chlorinated $C_6$ compounds (compounds (X)) will be contained.

After thus obtaining the composition (IIA) 6 and/or (IIB) 10, such composition (IIA) 6 and/or (IIB) 10 will be distilled in a distillation tower 2 (hereinafter referred to as the second distillation). In the composition (IIA) 6 (IIB) 10, the trans-isomer and the compound (X) are contained, and in some cases, coloring components, distillation residues, etc., may likely be contained.

In the second distillation, the compound (X) will be removed as a high boiling component 8, and the desired trans-isomer will be obtained as a low boiling component 7. It is preferred that components other than the trans-isomer will be removed as a high boiling component 8. Further, it is preferred that the low boiling component 7 will be obtained as a component from the top of the distillation tower 2.

In the second distillation, the distillation temperature is preferably from 20 to 120° C., more preferably from 60 to 80° C. The pressure (gauge pressure, the same applies hereinafter) is preferably from 0 to 1013 hPa, more preferably from 80 to 300 hPa. The second distillation is carried out usually by using the distillation tower 2. There is no particular limit to the theoretical plate number of the distillation tower 2. However, the second distillation can be carried out by a distillation tower having preferably from 1 to 20 plates, more preferably from 1 to 10 plates. Further, the second distillation system is not particularly limited, and it can optionally be carried out by e.g. a batch system or a continuous system.

By the process of the present invention, a less colored trans-isomer can be obtained, but it is preferably colorless. Further, its Hazen color number (APHA) is preferably at most 200, more preferably at most 100, still further preferably at most 20.

Here, the Hazen color number (APHA) is measured in accordance with ASTM D1209-1980 (American National Standards Institute). The color number standard liquid is prepared by dissolving 1.245 g of potassium hexachloroplatinum(IV) (0.500 g as platinum) and 1.000 g of cobalt(II) chloride hexahydrate (0.250 g as cobalt) in 100 ml of hydrochloric acid and further diluting the solution with distilled water to 1000 ml, which is used as a color number standard liquid having a Hazen color number of 500. Color number standard liquids having Hazen color numbers of 100, 50, 20 and 10 are ones prepared by diluting the color number standard liquid having a Hazen color number of 500 with distilled water 5, 10, 25 and 50 times, respectively. The Hazen color number is represented by the number of a color number standard liquid having the same tone as visually compared by putting a test sample in a test tube having a prescribed size (diameter: 3 cm, length: about 20 cm). One observed from the top surface of the test tube is represented by a Hazen color number (APHA). APHA is an abbreviation of American Public Health Association.

Further, by the process of the present invention, a trans-isomer of high purity can be obtained, and its purity is preferably at least 98%, more preferably at least 99%.

The process of the present invention is intended to obtain the trans-isomer, but if it is desired to obtain the cis-isomer, the low boiling component 4 containing the cis-isomer removed by distillation A and/or the low boiling component 9 containing the cis-isomer removed by distillation B, may be used, and by distillation in the same manner as distillation A or distillation B, the cis-isomer of high purity can also be fractionated.

The trans-isomer obtained by the process of the present invention and the cis-isomer obtainable as the case requires, can be used usefully as e.g. intermediates for pharmaceuticals or agricultural chemicals. The process of the present invention may be fully or partly carried out by a batch system or by a continuous system.

EXAMPLES

Now, the present invention will be described in detail with reference to Examples, but the present invention is by no means thereby restricted. Examples 1 to 3 are Working Examples of the present invention, and Example 4 is a Comparative Example. Further, the unit for % in the Table is mass % determined by gas chromatography. Further, % of the trans-isomer may also represents the purity of the trans-isomer.

Example 1

500 mL of a bottom having 3-chloropropene separated by distillation from the reaction product of propene with chlorine (the composition of the bottom is shown in the column for the bottom in Table 1), was subjected to batch distillation by a distillation tower of 50 plates under conditions of a distillation temperature of 60° C. and a pressure of 100 hPa. A composition comprising $C_3$ compounds and a cis-isomer in the bottom, was fractionated and removed as a low boiling component. And, in the batch distillation, 150 mL of a crude liquid comprising $C_6$ compounds and a trans-isomer, was obtained as a high boiling component.

Then, the crude liquid was mixed with chlorine gas in an amount of 1.2 times by mol of the $C_6$ compounds contained in the crude liquid, and chlorine was reacted to the crude liquid at 30° C. under atmospheric pressure. Thereafter, hydrogen chloride was removed by nitrogen. Then, this crude liquid was distilled by a distillation tower of 5 plates under conditions of a distillation temperature of 60° C. and a pressure of 100 hPa, to obtain 115 mL of the trans-isomer of high purity as a low boiling component. As analytical results by gas chromatography of the low boiling component, the recovery rate of the trans-isomer and the Hazen color number (APHA) are shown in Table 1.

Example 2

The same bottom as in Example 1 was supplied to a distillation tower of 30 plates at a rate of 100 mL/hr and continuously distilled under conditions of a distillation temperature of 60° C. and a pressure of 100 hPa. A composition comprising $C_3$ compounds and a cis-isomer in the bottom, was continuously fractionated and removed as a low boiling component. As a high boiling component of the distillation, a crude liquid was withdrawn at a rate of 30 mL/hr from the tower bottom.

Then, in the same manner as in Example 1, the crude liquid was mixed with chlorine gas in an amount of 1.2 times by mol of the $C_6$ compounds contained in the crude liquid, and chlorine was continuously reacted at 30° C. under atmospheric pressure. Thereafter, the crude liquid was passed through a granular sodium hydroxide-packed column to remove hydrogen chloride. Then, the passed crude liquid was distilled by a distillation tower of 5 plates under conditions of a distillation temperature of 60° C. and a pressure of 100 hPa, to obtain a trans-isomer of high purity as a low boiling component from the top of the tower at a rate of 23 mL/hr. As analytical results by gas chromatography of the low boiling component, the recovery rate of the trans-isomer and the Hazen color number (APHA) are shown in Table 1.

Example 3

The same bottom as in Example 1 was firstly mixed with chlorine gas in an amount of 1.5 times by mol of the $C_6$ compounds in the bottom, and chlorine was continuously reacted at 30° C. under atmospheric pressure. Then, the bottom was supplied to a distillation tower of 30 plates at a rate of 100 mL/hr and continuously distilled under conditions of a distillation temperature of 60° C. and a pressure of 100 hPa. A composition comprising $C_3$ compounds and a cis-isomer, was continuously fractionated and removed as a low boiling component. As a high boiling component of the distillation, a crude liquid comprising chlorinated $C_6$ compounds and a trans-isomer, was withdrawn from the tower bottom. Further, the obtained crude liquid was continuously distilled by a distillation tower of 5 plates under conditions of a temperature of 60° C. and a pressure of 100 hPa, to obtain a trans-isomer of high purity as a low boiling component from the top of the tower at a rate of 23 mL/hr. As analytical results by gas chromatography of the low boiling component, the recovery rate of the trans-isomer and the Hazen color number (APHA) are shown in Table 1.

Example 4

500 mL of the same bottom as in Example 1 was firstly mixed with chlorine gas in an amount of 1.5 times by mol of the $C_6$ compounds in the bottom, and chlorine was reacted at 30° C. under atmospheric pressure. And, hydrogen chloride was removed by nitrogen. Then, this bottom was subjected to batch distillation by a distillation tower of 50 plates under conditions of a distillation temperature of 60° C. and a pressure of 100 hPa. As a low boiling component, $C_3$ compounds or the like was fractionated and removed, and as a high boiling component, 290 mL of a crude liquid was obtained. Then, this crude liquid was distilled by a distillation tower of 5 plates under conditions of a distillation temperature of 60° C. and a pressure of 100 hPa. And, from the top of the tower, a component comprising a cis-isomer and a trans-isomer, was obtained as a low boiling component in an amount of 250 mL. Further, this low boiling component was distilled by a distillation tower of 50 plates at a distillation temperature of 60° C. under a pressure of 100 hPa, to obtain 113 mL of a trans-isomer as a high boiling component from the tower bottom. Distillation was carried out three times, but the obtained trans-isomer was distinctly colored, and it was apparently necessary to carry out an operation to remove the coloring components. As analytical results by gas chromatography of the high boiling component before removal of the coloring components, the recovery rate of the trans-isomer and the Hazen color number (APHA) are shown in Table 1.

TABLE 1

| Components | Tower bottom liquid | Ex. 1 | Ex. 2 | Ex. 3 | Ex. 4 |
|---|---|---|---|---|---|
| $C_3$ compounds (%) | 43 | — | — | — | — |
| cis-isomer (%) | 27 | 0.1 | 0.1 | 0.1 | 0.1 |
| trans-isomer (%) | 24 | 99.8 | 99.5 | 99.5 | 99.5 |
| $C_6$ compounds (%) | 6 | 0.1 | 0.4 | 0.4 | 0.4 |
| Recovery rate of trans-isomer (%) | — | 96.5 | 95.2 | 94.3 | 94.3 |
| Hazen color number (APHA) | — | 10 | 10 | 10 | 500 |

INDUSTRIAL APPLICABILITY

By the process of the present invention, it is possible to obtain a less colored trans-isomer in high purity, which is useful as e.g. an intermediate for pharmaceuticals, an intermediate for agricultural chemicals or an intermediate for functional materials. Further, by the process of the present invention, the trans-isomer of high purity can be obtained by the two distillation operations and one step of reacting chlorine or bromine, whereby the production process can be substantially shortened. In the process of the present invention, the obtained trans-isomer is separated as a low boiling component, and accordingly, it is possible to obtain the trans-isomer of high purity with a less color and free from a distillation residue, without further distillation or discoloration by an adsorber such as activated carbon. The process of the present invention is a process which is capable of producing the trans-isomer in a large amount and which involves a small number of steps without requiring any special operation. Accordingly, it is an excellent process suitable for industrial operation.

The entire disclosure of Japanese Patent Application No. 2000-293918 filed on Sep. 27, 2000 including specification, claims, drawings and summary is incorporated herein by reference in its entirety.

What is claimed is:

1. A process for producing trans-1,3-dichloropropene of having a Hazen color number (APHA) of at most 200, which comprises distilling the following composition (II) obtainable from the following composition (I), to remove a component containing chlorinated or brominated $C_6$ compounds (compounds X), as a high boiling component, and to obtain trans-1,3-dichloropropene having said APHA as a low boiling component:

Composition (I): A composition comprising cis-1,3-dichloropropene, trans-1,3-dichloropropene and $C_6$ compounds;

Composition (II): A composition which is the following composition (IIA) and/or the following composition (IIB);

Composition (IIA): A composition which is obtainable by distilling the composition (I) to remove a low boiling component containing cis-1,3-dichloropropene and then reacting chlorine or bromine to the residual high boiling component, and which comprises trans-1,3-dichloropropene and chlorinated or brominated $C_6$ compounds (compounds X);

Composition (IIB): A composition which is obtainable by reacting chlorine or bromine to the composition (I), followed by distillation to remove a low boiling component containing cis-1,3-dichloropropene, and which comprises trans-1,3-dichloropropene and chlorinated or brominated $C_6$ compounds (compounds X).

2. The process according to claim 1, wherein the composition (I) is a reaction product of propene with chlorine, or a residue having 3-chloropropene removed from such a reaction product.

3. The process according to claim 1, wherein the composition (I) further contains 1,3-dichloropropane.

4. The process according to claim 1, wherein the compounds (X) are chlorinated $C_6$ compounds.

5. The process according to claim 1, wherein the composition (II) is the composition (IIA).

6. The process according to claim 1, which includes a step of further distilling the low boiling component containing cis-1,3-dichloropropene, removed in the step of obtaining the composition (II), to fractionate cis-1,3-dichloropropene.

7. Trans-1,3-dichloropropene having a Hazen color number (APHA) of at most 200.

8. The trans-1,3-dichloropropene of claim 7, having an APHA of at most 100.

9. The trans-1,3-dichloropropene of claim 7, having an APHA of at most 20.

10. The process according to claim 1, wherein the APHA is at most 100.

11. The process according to claim 1, wherein the APHA is at most 20.

12. A process for producing trans-1,3-dichloropropene, which comprises distilling the following composition (IIA) obtainable from the following composition (I), to remove a component containing chlorinated or brominated $C_6$ compounds (compounds X), as a high boiling component, and to obtain trans-1,3-dichloropropene as a low boiling component:

Composition (I): A composition comprising cis-1,3-dichloropropene, trans-1,3-dichloropropene and $C_6$ compounds;

Composition (IIA): A composition which is obtainable by distilling the composition (I) to remove a low boiling component containing cis-1,3-dichloropropene and then reacting chlorine or bromine to the residual high boiling component, and which comprises trans-1,3-dichloropropene and chlorinated or brominated $C_6$ compounds (compounds X).

13. A process for producing trans-1,3-dichloropropene, which comprises distilling the following composition (IIB) obtainable from the following composition (I), to remove a component containing chlorinated or brominated $C_6$ compounds (compounds X), as a high boiling component, and to obtain trans-1,3-dichloropropene as a low boiling component:

Composition (I): A composition comprising cis-1,3-dichloropropene, trans-1,3-dichloropropene and $C_6$ compounds;

Composition (IIB): A composition which is obtainable by reacting chlorine or bromine to the composition (I), followed by distillation to remove a low boiling component containing cis-1,3-dichloropropene, and which comprises trans-1,3-dichloropropene and chlorinated or brominated $C_6$ compounds (compounds X).

14. The process according to claim 12, wherein the purity of trans-1,3-dichloropropene is at least 98%.

15. The process according to claim 12, wherein the purity of trans-1,3-dichloropropene is at least 99%.

16. The process according to claim 13, wherein the purity of trans-1,3-dichloropropene is at least 98%.

17. The process according to claim 13, wherein the purity of trans-1,3-dichloropropene is at least 99%.

* * * * *